(12) United States Patent
Koster (10) Patent No.: US 8,543,411 B2
(45) Date of Patent: Sep. 24, 2013

(54) SYSTEMS AND METHODS FOR DETECTING COUNTERFEIT PHARMACEUTICAL DRUGS AT THE POINT OF RETAIL SALE

(75) Inventor: Karl H. Koster, Atlanta, GA (US)

(73) Assignee: United Parcel Service of America, Inc., Atlanta, GA (US)

( * ) Notice: Subject to any disclaimer, the term of this patent is extended or adjusted under 35 U.S.C. 154(b) by 2689 days.

(21) Appl. No.: 10/702,253

(22) Filed: Nov. 5, 2003

(65) Prior Publication Data

US 2005/0108044 A1    May 19, 2005

(51) Int. Cl.
*G06Q 50/00*    (2012.01)

(52) U.S. Cl.
USPC ................... 705/2; 705/3; 340/5.8

(58) Field of Classification Search
USPC ...................... 705/2–3; 340/5.8
See application file for complete search history.

(56) References Cited

U.S. PATENT DOCUMENTS

| | | | |
|---|---|---|---|
| 6,935,560 B2 * | 8/2005 | Andreasson et al. | 235/385 |
| 2003/0074223 A1 * | 4/2003 | Hickle et al. | 705/2 |
| 2003/0160698 A1 * | 8/2003 | Andreasson et al. | 340/573.1 |
| 2003/0164401 A1 * | 9/2003 | Andreasson et al. | 235/385 |
| 2003/0216969 A1 * | 11/2003 | Bauer et al. | 705/22 |
| 2004/0008123 A1 * | 1/2004 | Carrender et al. | 340/825.49 |
| 2004/0046020 A1 * | 3/2004 | Andreasson et al. | 235/385 |
| 2005/0075145 A1 * | 4/2005 | Dvorak et al. | 455/572 |
| 2007/0176773 A1 * | 8/2007 | Smolander et al. | 340/539.26 |

\* cited by examiner

*Primary Examiner* — Sind Phongsvirajati
(74) *Attorney, Agent, or Firm* — Alston & Bird LLP (57) ABSTRACT

A system including capabilities for identifying, authenticating and/or tracking pharmaceutical drugs contained in a package from the point of manufacture to the point of retail sale or dispensing. One embodiment utilizes radio frequency (RFID) tags imbedded into the packaging, the RFID tags containing information identifying at least the package to the manufacturer of the package. A computer system uses an encryption algorithm to produce a machine readable indicia affixed to the packaging after the contents are sealed. Thereafter, various systems can read the RFID tag and the encrypted data at various points in the supply chain and may initiate a query to a manufacturer's database to determine whether the packaging and encrypted data match values stored in the database. This can be used in part to verify the authenticity of the package as well as indicate other functions affecting the sale of the package or dispensing the contents.

17 Claims, 10 Drawing Sheets

SYSTEMS AND METHODS FOR DETECTING COUNTERFEIT PHARMACEUTICAL DRUGS AT THE POINT OF RETAIL SALE

FIELD OF THE INVENTION

This invention relates to authenticating packaged goods after their manufacturing in order to detect counterfeited goods. Specifically, a method of authenticating a sealed package of pharmaceutical drugs is disclosed allowing detection of counterfeit drugs, as well as tracking and reporting of manufactured drugs along the supply chain up to the point of sale or dispensing.

BACKGROUND

The rising prices of various pharmaceutical drugs is a major topic of concern in the U.S. healthcare system. The impact of rising drug prices has been documented and reported in recent years. One impact includes the marketing of counterfeit drugs. Counterfeit drugs is an increasing problem given the ever increasing retail prices of various newly developed drugs. Further, it is difficult to detect whether a pharmaceutical substance is authentic or counterfeit without expensive laboratory equipment and extensive testing. A tablet manufactured from paste looks identical to an advanced cancer fighting drug. Similarly, water-based solutions look similar to sophisticated drugs in liquid form. Not surprisingly, various criminal elements are beginning to manufacture counterfeit drugs and introducing them into the supply chain to gain quick and huge profits.

In the U.S., marketing of drugs has been historically closely regulated. The regulation of the delivery of drugs from the manufacturer to the retailer makes it difficult to introduce counterfeit drugs. However, the supply chain has been recently impacted by the introduction of the Internet. Various web sites now offer drugs directly to consumers, and there is no guarantee of the quality or authenticity of the drugs. In fact, the ability of U.S. consumers to purchase drugs from Canada and other countries using the Internet, as well as by crossing the border, is an area of recent intense public debate. Lower costs of the identical drug in other countries has motivated U.S. consumers to use the Internet to purchase drugs from foreign pharmacies. Issues of public safety and drug quality are a concern to both the U.S. government and the drug manufacturers. Instances have been detected where counterfeit drugs were sold and passed off as legitimate life saving drugs, thus eroding public confidence in the drug delivery infrastructure.

Further, the globalization of trade often results in many drugs being manufactured in other countries and readily available in almost any part of the world. A drug manufacturing plant in a third world country may not have stringent quality and security controls, and drugs may be improperly imported and introduced into the U.S. supply chain as a genuine, domestic manufactured pharmaceuticals. Absent differences in the packaging, it can be difficult to distinguish genuine drugs from counterfeit drugs. Further, it is easy for counterfeiters to copy the packaging so that the average consumer cannot tell the difference between legitimate goods and counterfeit goods.

The ever increasing price of various pharmaceutical drugs, the increasing desire of consumers to obtain various drugs at lower prices, the ubiquitous offers for drugs promised at a lower cost over the Internet, the ease of which counterfeit pharmaceuticals can be smuggled into the U.S., all lead to the increasing problem of counterfeit drugs being introduced into the pharmaceutical supply chain.

Further complicating the picture is the possibility of terrorists deliberately causing massive public disruption in the U.S. healthcare system by attempting to introduce counterfeit drugs, not only for profit motive, but for terroristic motives. Past events where over-the-counter drugs were adulterated caused immense public concern (e.g., filling Tylenol tablets with cyanide). The introduction of counterfeit drugs would significantly weaken consumer confidence in legitimate and authentic drugs.

All these factors lead to the need for a system of tracking pharmaceuticals from the factory, along the supply chain, to the point of sale or dispensing, where the authenticity of the goods can be verified by various entities in the supply chain. Further, there is a need to indicate any condition that relates to the safety and purity of the drugs.

SUMMARY

These and other benefits are realized in the present invention that uses radio frequency identification tags along with encrypted data on the packaging to identify and authenticate a sealed package purporting to contain pharmaceuticals of a certain type.

Packages are manufactured containing either embedded or attached RFID tags for identifying a package. The RFID tags are typically written or programmed with a unique numerical value, which can be random or sequential, that is used to identify the package. At the time of manufacture, when the package is filled and sealed by the pharmaceutical company, the RFID tag is read by the manufacturer and associated with various manufacturing data, including data pertaining to the drug contained in the package. The manufacturing data typically includes information about the lot, date of manufacture, place of manufacture, drug composition, etc. Only the manufacturer knows the manufacturing information associated with a given RFID tag. Further, the RFID tag value serves as input to an encryption algorithm that produces authentication data subsequently used to authenticate the package. The authentication data is stored in a manufacturing record contained in a manufacturing database and indexed by the package identifier value.

Because the RFID tag by itself may not describe the drug, and the encrypted authentication key by itself does not itself describe the drug, the combination of both pieces of information by themselves, without any other data, does not describe the contents of the package. Typically, only the manufacturer knows the correct authentication key. If just prior to the sale or dispensing of the package the identification and authentication data values are read and communicated to the manufacturing database, the database can then indicate whether the two pieces of information match. If the information matches the package identifier and authentication data in the database, the package likely did originate from the manufacturer. Further, the manufacturer could report the contents of the package for authentic packages. Specifically, the manufacture could indicate the particular drug indicated in the package. The reported indication of the package contents would be checked at sale or dispensing with the package label to ensure that the reported package contents matches the description on the label affixed to the package. Assuming that the integrity of the seal on the package is maintained, the package and its contents can be assumed to be authentic.

Although a counterfeiter may be able to obtain RFID tags, the counterfeiter is unlikely to obtain values that are known to be in the database of the manufacturer. Further, the counterfeiter is unlikely to know the encryption algorithm used by a particular manufacturer for that particular RFID tag value to determine the authenticating data. It is expected that manufacturers will periodically change their encryption algorithms. Finally, even if the algorithm is known, it is unlikely that a counterfeiter would know what to print on the label of the package and describe the drug within the package with the same information as provided by the manufacturer when authenticating the package. Thus, it is unlikely that a counterfeiter could manufacturer a package of drugs without it being detected as counterfeit.

One way a package could contain counterfeit drugs is if an actual package was stolen en route along the supply chain and the contents tampered with, and the original package resealed and reintroduced into the supply chain. This likelihood is diminished by the use of RFID tags facilitating identification of the goods along the supply chain, and increasing the likelihood of detecting missing inventory. Missing inventory can be reported to the manufacturer and recorded as such in the manufacturing database according to the reported missing RFID tag values. Once the missing packages are reintroduced into the supply chain, the package identification values are checked against the manufacturer's database and reported at the point of sale or dispensing indicating that the packaging, though authentic, should not be sold or dispensed.

In this manner, packages goods can be better tracked along the supply route and authenticated at any point including at the point the packaging is opened for preparation for sale or dispensing. Further, should legitimate packages be diverted in the supply chain, they can be easily detected and flagged in subsequent transactions. This allows a manufacturer to track the distribution of packages.

DETAILED DESCRIPTION

As required, a detailed illustrated embodiment of the invention is disclosed herein. However, the operating structures and processes associated with the illustrated embodiment of the invention may be altered in other embodiments, in a wide variety of forms, some of which may differ significantly from the disclosed embodiment. Consequently, the specific structural and functional details disclosed herein are merely representative; yet in that regard they are deemed to afford the best embodiment for disclosure and to provide a basis for the claims herein, which define the scope of the present invention.

The present inventions will now be described more fully with reference to the accompanying figures, in which some, but not all embodiments are shown. In various figures, similar elements are illustrated multiple times, but are not necessarily numbered in every instance so as to make the figures easier to comprehend. Like numbers refer to like elements throughout the figures.

In order to fully appreciate the various applications of the present invention for the detection and reporting of a package or item of commerce that is counterfeit, the following embodiment is provided in the context of detecting counterfeit pharmaceuticals or those that are suspect for other reasons. However, the principles of the present invention are not limited only to application to pharmaceutical drugs. Although the principles may be applied to products in a supply chain, the application to pharmaceutical drugs is sufficient to illustrate the principles of the present invention.

Figure 1:
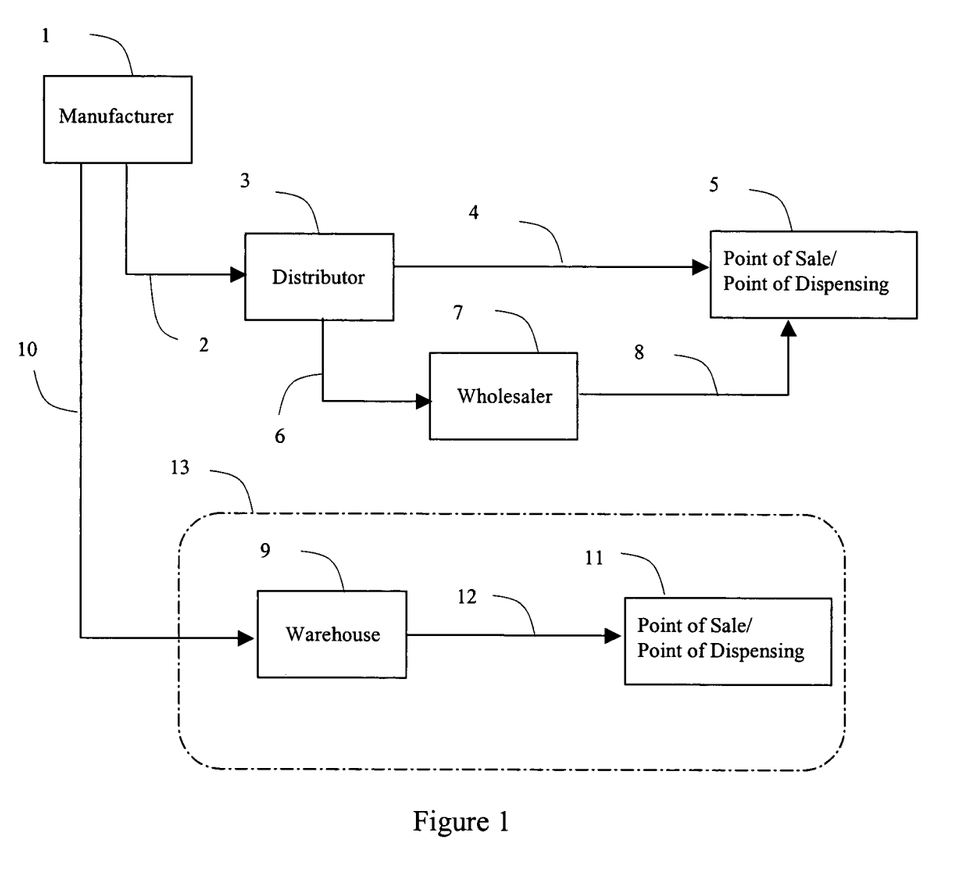
FIG. 1 illustrates a potential supply chain according to the prior art.

A brief overview of an exemplary supply chain for pharmaceuticals is presented in FIG. 1. In FIG. 1, a pharmaceutical manufacturer 1 is at the beginning of the manufacturing supply chain of drugs. As used herein, there is no distinction between the terms 'pharmaceutical' and 'drug' unless otherwise stated. Although many embodiments are illustrated herein using 'prescription' drugs, the principles of the present invention applies to 'over the counter' drugs as well. The manufacturer may deliver bulk shipments to a drug distributor 3. The distributor 3 resells the drugs either to a point of sale ("POS"—e.g., retailer) or point of dispensing ("POD"—e.g., hospital or doctor's office) 5 directly, or alternatively, the distributor 3 may sell the drugs to a wholesaler 7. The wholesaler, in turn, sells the drugs to the POS/POD. The selection of which branch in the supply chain is used depends on a variety of factors, including geographical relationship, size and amount the purchases, etc. Examples of POD/POS include independent retail pharmacies, buying groups, hospital pharmacies, doctor's offices, etc. The POD/POS is the termination of the supply chain and typically represents the last point where authentication of the drugs in the supply chain can effectively occur prior to use.

Alternatively, the manufacturer 1 may sell the drugs directly to a large retail chain pharmacy, or to a large retailer providing in-store pharmacy departments (e.g., national grocery store chain offering an in-store pharmacy). In this case, the manufacturer 1 may ship the drugs directly to the retailer's internal warehouse 9. The retailer than arranges for shipping the drugs to various POD/POS 11 operated by the retailer. As indicated by the dotted line 13, the retailer operates the warehouse 9 and the POD/POS 11.

The methods of shipping the drugs among the various entities are pertinent. Typically, shipping from the manufacturer 10, 2 may include trucking, common carrier, freight, or other public or private transportation means. Similarly, the distributor and wholesaler may ship 4, 6, 8 in a similar method, including common carriers specializing in parcels, packages and so forth. Finally, the postal service can be used as well. The shipping of drugs from the warehouse 9 to the POS/POD 11 along a route 12 may involve private contracted freight trucks that are operated by the retailer for delivery of general retail merchandise.

Along any path 2, 4, 6, 8, 10, 12 the contents of a drug shipment can be diverted, lost, substituted, tampered, replaced, or stolen. Further, the controls and checks performed along the various routes and by the various entities and/or persons handling the drugs may not be enforced, resulting in a failure to detect loss or tampering. The actions typically defined for handling and accounting for the drugs may depend on the type of drugs being shipped. For example, class II drugs (including codeine, morphine, etc.) are typically more carefully controlled and accounted for, recognizing the desirability of such drugs for illicit purposes. The same controls and accounting procedures are typically not provided for other drugs, such as class III drugs. However, many of the class III drugs are quite valuable in regard to economic value and may be the target of counterfeiting.

The importance of detecting counterfeit drugs is important for any class of drugs. Likewise, the controls for tracking, authenticating, detecting authentic drugs is also equally important for all classes. It is desirable that these controls can be utilized at any point of the supply chain. Security measures relying on a sequence of previously performed procedures during the handling of the drug are inherently uncertain because a current person can never be certain of the previously occurring events. Specifically, a POD/POS 5 should be able to authenticate a package regardless of whether the drugs were handled by a wholesaler 7 in the supply chain or not. In some instances, the drugs may have been properly delivered to the POD/POS, but then the drugs may be found missing. Further, if a quantity of drugs are diverted by legitimate export to another county and then reintroduced into the U.S. supply chain, the POD/POS should be able to verify the drugs as authentic, regardless of where they re-entered the domestic supply chain. This is accomplished in part by the manufacturer maintaining control of a database allowing the distributor 3, the wholesaler 7, the POD/POS 5, 11 and personnel at the warehouse locations 9 to authentic a package for any reason and at any time. Typically, authentication is most important at the POD/POS since that is the last point at which the drugs can be controlled prior to use by the user.

A variety of events or actions can be detected at any of the distribution points by querying the manufacturer's database. For example, if the manufacturer should discover subsequent to manufacturing that some drugs are defective, these packages can be flagged as such in the database and indicated as such in response to an authentication request from the POD/POS. Should certain shipments be lost or stolen, the expected recipient of the shipment could inform the manufacture of the loss, and the manufacturer could flag the items in the database so that they could be detected if they are improperly re-introduced into the supply chain. Further, should counterfeit drugs be introduced into the supply chain using the same package identifiers, these values would be flagged in the manufacturing database and reported as such upon requesting authentication at the POS/POD.

Figure 2:
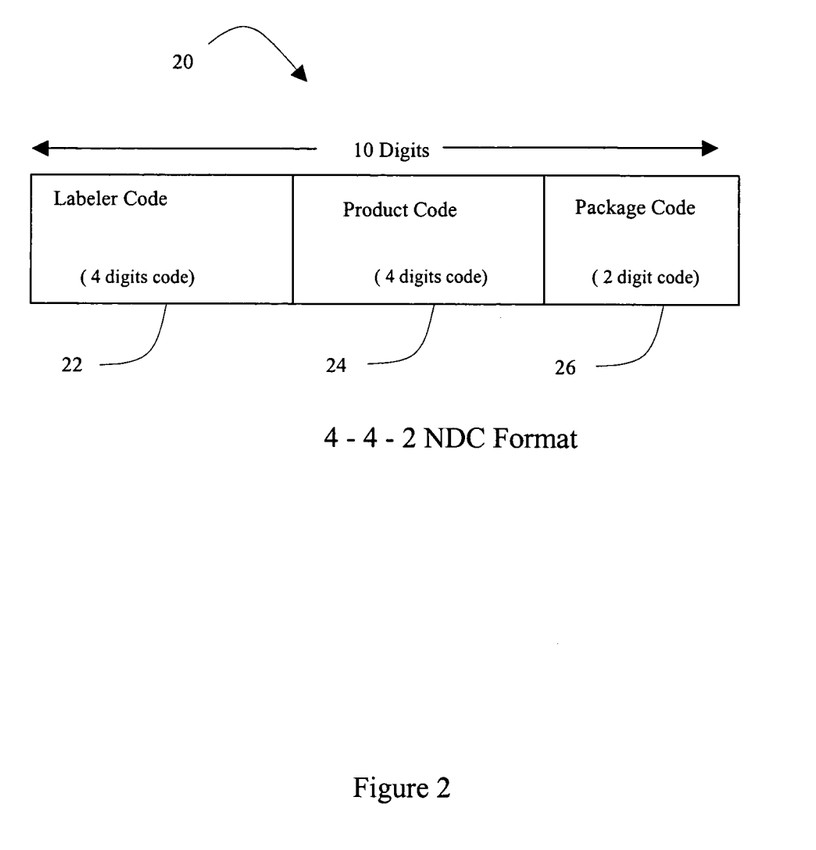
FIG. 2 illustrates one embodiment of the structure of the national drug code indicia according to the prior art.

Currently, drugs are identified in part by using the National Drug Code (NDC). There are various embodiments of the NDC and one format is illustrated in FIG. 2. The NDC is a typically a 10 digit value that is typically encoded using a one-dimensional bar code on the package that is scanned using commercial available bar code scanners. The structure of the NDC code 20 has different formats, and may be structured in a 4-4-2 format, a 5-3-2 format, or a 5-4-1 format. FIG. 2 illustrates the involves a 4-4-2 format comprising a four digit labeler code 22, followed by a four digit product code 24, and a two digit package code 26. The labeler code identifies an entity that manufactures, re-packs, or distributes the drug. The value is assigned by the Food and Drug Administration. The product code identifies the strength, dosage, and formulation of the contents. The package code identifies the package size. Both the product code and the package code are determined by the labeler. There are other variations of the NDC formats, such as an 11 digit form, which is used by various government agencies that involve pre-pending a zero in front of the labeler code. Regardless of the format, each is well defined and known in the industry.

By optically scanning a package's NDC code, inventory systems can be quickly updated and other systems can identify the contents of the package. The NDC code, however, is well known, and the information is not encrypted in any way and is not intended to be a security mechanism. Examination of a package's label allows codes to be reversed engineered and duplicated on a counterfeit package purporting to contain the same type of drug from the same manufacturer. The NDC code is not intended to be a security measure. Nor does the NDC code identify a particular package. Thus, there are no procedures from discouraging or thwarting unauthorized parties from creating a counterfeit package based on replicating the NDC value.

Figure 3:
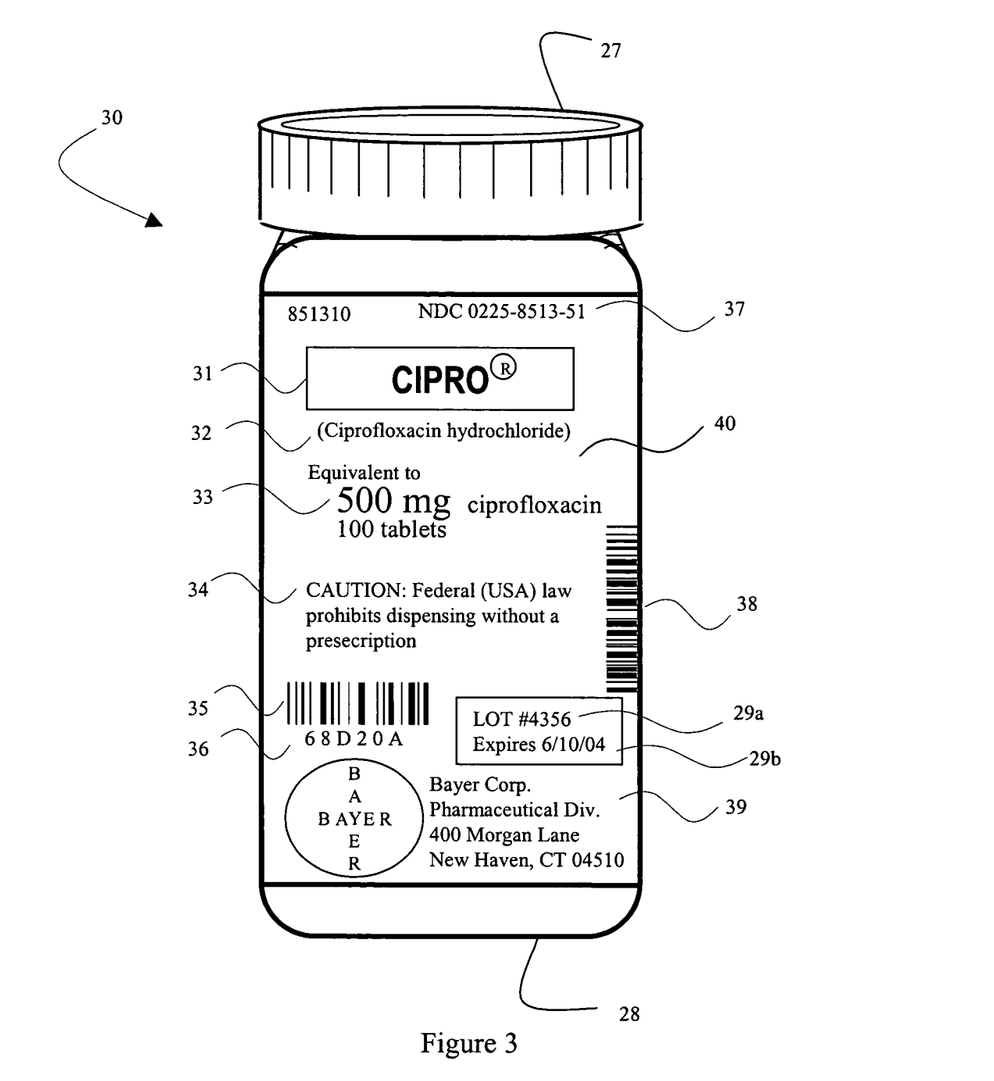
FIG. 3 illustrates one embodiment of a sample label including indicia in accordance with the principles of the present invention.

FIG. 3 illustrates one embodiment of a label on a package according to the principles of the present invention. FIG. 3 illustrates a container 30 comprising a bottle with a screw cap 27 and having a label 40 affixed to the bottle 28. The label 40 contains information that is required by federal labeling laws and information added for marketing motivations. In FIG. 3, the brand name, CIPRO® 31 is displayed with the generic formula 32. The package indicates the quantity (500 tablets) 33 with appropriate labeling 34 indicating the contents can be only dispensed with a prescription. Typically, the name and trademark 39 information of the manufacturer is provided, as is a barcode 38 that provides a machine-readable version of the national drug code. The national drug code is also provided in numerical form 37.

The bottle also contains information that is unique to the specific package, namely lot or batch information, such as indication of "Lot 4356" 29a and the expiration date of the drugs, which is this embodiment is "6/10/04" (Jun. 10, 2004) 29b. There may be numerous packages associated with the particular lot number. The expiration date provides a visual indication of when the medication expires, allowing the user or person dispensing the drug to verify its expiration date. The expiration information is further associated by the manufacturer with the batch information in a database. The lot and expiration information is typically not printed on the labels beforehand, since the information is not known until the contents are filled. Thus, the lot or batch information is typically provided on the label at filling, or just prior or after filling. Typically, the information is embossed on to the label and cannot be easily altered.

The embodiment of FIG. 3 also includes a second bar code 35 representing the authenticating data. (The bar codes of FIG. 3 are for illustrative purposes only and do not correspond to industry standard bar code representations.) In this embodiment, an alphanumeric representation 36 of the authenticating data is displayed near the bar code. This facilitates inputting the authenticating data should the bar code become unreadable or the bar code scanner nonfunctional. Although six alphanumeric characters are illustrated, other embodiments may use more or less digits. In general, the longer the values, the more difficult it is to circumvent the scheme.

FIG. 3 does not illustrate the RFID tag, since this is typically affixed under the label, inside the container, or affixed to the container in some other location or manner so that it is not readily exposed or visible. By placing the RFID tag in a protected location, the tag is unlikely to be damaged during the course of normal handling. Further, the package is typically sealed using various tamper resistant means known in the art of packaging, including clear plastic shrink wrap or foil covering the container's opening (which is not shown as it is underneath the cap).

Although FIG. 3 illustrates a container, the label may be affixed to a variety of packages, including bottles, jars, boxes, cardboard containers, envelopes, and other forms for conveying pharmaceuticals, including bubble plastic tablet holders. Any of these other variations are within the scope of the term 'package' as used herein. Further, the label may be printed directly onto the package, or a separate plastic, foil, or paper member and affixed using adhesion, glue, fused, shrink-wrap means, or other means for attachment.

Figure 4:
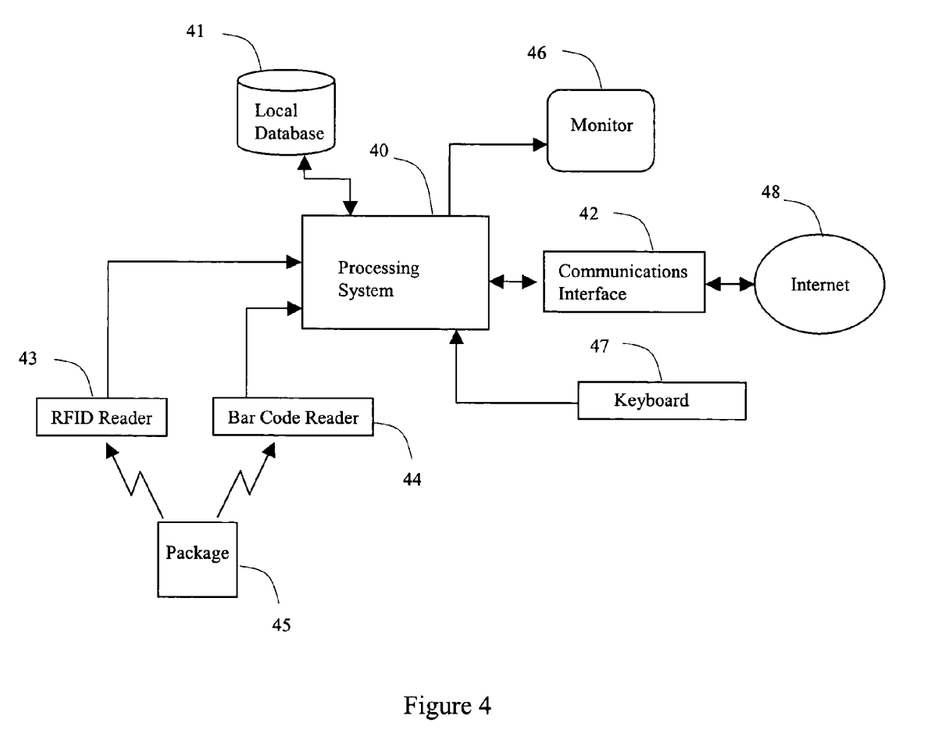
FIG. 4 illustrates one embodiment of a system used for reading package identifiers and querying a manufacturer's authentication database in accordance with the principles of the present invention.

The indicia associated with the package as illustrated in FIG. 3 is typically 'read' at the point of sale or point of dispensing in conjunction with the authentication process. The system for reading the package is illustrated in FIG. 4. FIG. 4 illustrates some of the functional components that are present in a POD/POS reading device. The device typically comprises a processing system 40 that may be based on a PC system, including processor, memory, and various input/output controllers, including various disk storage devices. The processing system 40 interfaces with a local database 41 that may be implemented on a hard disk system integrated with the processing system 41 or on a separate device. The database is typically under the control of an database program application, as is well known by those skilled in the art. Typically, the local database 41 is used to maintain historical records for recording packages that are scanned. The local database may also be integrated into an inventory management system or a point of sale system. The database maintains a historical record of packages scanned for the purpose of allowing subsequent review. Such a record can be useful to verify that a package was sold or dispensed, checked for authenticity, or that the package was checked prior to sale or dispensing. The manufacturing database maintains information pertaining to any such flags reported impacting the use of the drug.

The processing system 40 interfaces with two input devices for "reading" a package. "Reading" as used herein broadly refers to any device processing and recognizing a machine readable indicia, signal, or other indication for automatic detection of a value. Two indicia are illustrated in this embodiment—the RFID tag represents the package identifier and the optical bar code represents the authentication data. The authentication data is determined by using the package identifier as input to a known encryption algorithm. Typically, only the manufacturer knows the encryption algorithm.

The RFID reader 43 is an input device that is able to detect a package identifier value associated with an RFID tag. The technology for such readers is well known and the RFID tag reader may incorporate a processor and embedded circuitry and software. The RFID reader may involve transmitting a low power radio signal directed to the RFID tag resulting in the RFID tag emanating a return signal that is processed by the reader to identify a numerical value. This is referred to as a 'passive' RFID tag and other types, such as active RFID tags can be used. Typically, the RFID tag provides a multi-digit value and the length associated of the value can be quite large (e.g., 32 bytes, 64 bytes, or more). Typically, the RFID tag reader provides the corresponding value as a digital binary number to the processing system 40. Similarly, the processing system 40 interfaces with a scanner or optical bar code reader 44. Although indicated as a bar code, the optical code could be a two dimensional optical code or other optical indicia. The bar code reader typically comprises a processor, additional circuitry, a light source, detector and embedded software. Typically, the bar code reader provides the corresponding digital value in binary form to the processing system 40. The principles of the present invention are not limited to a RFID reader or optical reader, but could function with any machine readable indicia, including magnetic encoded strips or ink, optical character recognition, or proprietary recognition schemes. Further, it is not required that two different technologies may be used. Both indicia could be conveyed by optical codes or RFID codes, including read/writable RFID tags, or some other means. The incorporation of RFID tags is disclosed as one embodiment as it allows packages to be easily manufactured incorporating tags. The bar code, representing the authentication data, however, cannot be determined until the package identifier tag value is known.

The RFID tag may be prominently affixed to the package so that it can be readily observed (but protected). Or the RFID tag may be embedded or affixed so that it is not readily observed. Typically, the placement of the RFID tag inside the package, for example, does not hinder the operation of reading the value. The optical bar code, however, typically must be visible for ready scanning by the bar code reader 44.

The lengths of the package identifier value and the authentication data is not limited to a specific value. In general, the longer the values, the greater the security provided. A larger package identifier increases the number of packages that can be uniquely identified. However, the longer the values, the greater the storage requirements imposed on the system and the processing for computing the authentication value.

The RFID tag may be determined solely by the package manufacturer, or by agreement with the pharmaceutical manufacturer. The RFID tag should be unique. It can be a random value, but typically is a sequential value from package to package. Replicated values should be avoided, since it may result in identical authenticating data causing multiple packages to appear identical. The RFID tags could be viewed as a 'flat numbering space', i.e., a single number without any sub-structure. Alternatively, sub-fields could be defined and portions could be used for identification of inventory, product, identifying the manufacturer, or indicating manufacturing information. Since RFID tags can contain much data, it is possible to use a portion of the RFID numbering space for such information and still maintain a sufficiently large package identifier number space. This would allow a portion of the RFID tag space to be used for other applications, such as product identification or indicating the NDC at the point-of-sale terminal.

Returning to FIG. 4, the processing system 40 also interfaces with a communications interface 42 that provides connectivity to the Internet 48. Typically, the processing system launches a query to a specific database including the package identifier and the authenticating data. Typically, the query is launched using an HTML of XML based query to an Internet web site operated by the pharmaceutical manufacturer. In many embodiments, a secure protocol, such as SSL may be used for added security. The Internet address used to identify the destination (e.g., directly or indirectly identifying the manufacturing database) may be determined by examining a portion of the RFID tag value. Alternatively, the manufacturer's database can be determined from a separate machine readable indicia, such as from the national drug code, and the address determined from a table lookup. Alternatively, the Internet address could be manually determined by the user based on the manufacturer indicated on the label. The communications interface may be integrated into the processing system, and may be based on a variety of technologies providing access to the Internet. Once the query is received at the web site, the information is relayed to the manufacturing database.

Finally, the processing system 40 interfaces with a computer display monitor 46 and a keyboard 47. The keyboard allows the user to manually key in a number, should the indicia be replicated in text form and the machine readable indicia unreadable. Alternatively, other technologies such as speech recognition could be used for providing input. The monitor may also be used to display the result of the query from the manufacturer's database, including a text message indicating that the package is authenticated or not, as well as any indications effecting the sale or dispensing of the drug. Typically, if the package is determined to be authentic, the response to the query also displays text information pertaining to the product. This information should correspond to the label on the package being authenticated.

The processing system may be embodied in a dedicated personal computer, with a separate bar code and RFID tag reader interfaced to the personal computer. Another embodiment incorporates the functionality of both readers in a dedicated handheld scanner that communicates with a server using a wireless LAN capability such as "bluetooth" or the various IEEE 802.11 (e.g., 802.11b) wireless based LAN protocols. The server would then access the Internet using well known wireline based interfaces. Alternatively, the above functions may be embodied by a point-of-sale device adapted for such functionality. Any of these or other physical embodiments are within the scope of the invention.

Figure 5:
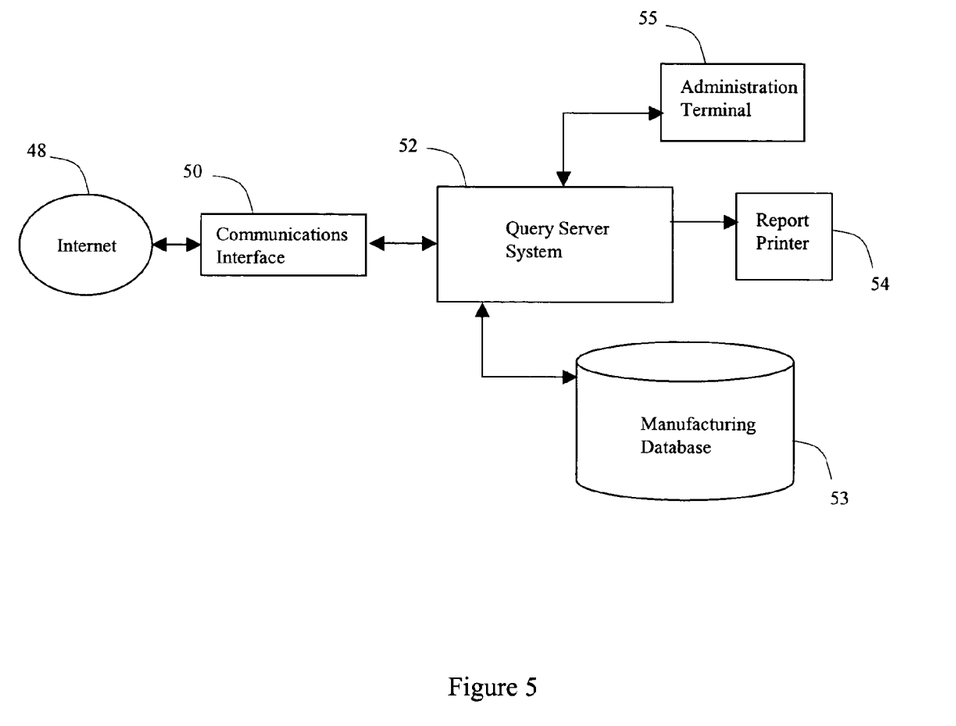
FIG. 5 illustrates one embodiment of the authentication database server in accordance with the principles of the present invention.

One embodiment of the system receiving the query originating from the POD/POS is illustrated in FIG. 5. The system is based on a computer server 52 that processes a large number of simultaneous queries. Such transaction processing systems are well known in the art and may employ parallel processors to provide the necessary query handling capacity and/or reliability. Not shown is the memory usually associated with such systems for storing queries while data is accessed; this is assumed to be integrated into the server 52. The server system typically accesses a database, which in this embodiment is the manufacturing database 53. The manufacturing database 53 stores records for each of the packages filled, including at least manufacturing data, the package identification value, and the corresponding authentication value. Typically, additional information is included. The manufacturing database may be populated by another computer system (not shown) that computes the authentication data and provides the manufacturing data. The query server system 52 (in this embodiment) accesses the manufacturing database so as to indicate whether the package is authenticated or not, and report any additional flags in the manufacturing database record effecting the sale or dispensing of the product. Other embodiments may incorporate additional functionality in the database, including providing drug interactions, warnings, or other medical or manufacturing information.

The queries at the server 52 are typically received over a communications interface 50 that in turn interfaces with the Internet 48. Although other communication networks and interfaces could be used, the relative ubiquity of the Internet facilitates communication with most point of sale and point of dispensing locations. The query server 52 also is typically connected to an administration terminal 55. The administration terminal 55 allows personnel, typically under the control of the pharmaceutical manufacturer, to alter information in the manufacturing database as required. For example, in the situation that a particular drug lot is found defective after manufacturing and distribution, or otherwise requiring recall, the administration terminal 55 can be used to access a database management program allowing flags to be set in the manufacturing database 53 for the specified manufacturing record(s). In this manner, when the server receives an authentication request for a package associated with a defective lot, the server may contine and authenticate the package, but indicate that the contents are subject to recall and should not be dispensed or sold. Similarly, the administration terminal 55 can be used to flag certain packages as being stolen, reported missing, or obtain reports regard abnormal conditions, such as when the drugs have exceeded their shelf life or expiration data, or if an inordinate number of queries are received from a single POD location.

When the manufacturing database receives a query, it typically records an indication of such, including each package identification value. Thus, once a package is authenticated, the record for the package identifier is flagged in the database. It is possible at the POS/POD can initiate authentication queries independent of the sale of the package, as well initiating an authentication query associated with the sale of the package. This could be accomplished by defining a query with an indication from the POD/POS as to whether the package is being sold in conjunction with the authentication procedures, or whether the package is simply being authenticated without being sold or dispensed. Any abnormal conditions, such as selling the same package repeatedly can be detected in the manufacturing database. Such a detected event may result in a response to the POD/POS instructing the person to carefully check the package and check for evidence of tampering. Thus, the manufacturing database can detect a package that has been recorded as previously sold. The system can also detect the originating entity, so that a complete record of all queries from an originating entity can be maintained.

Finally, the server system 52 is also connected to a report printer that can be used to print out various reports that may be initiated by the administration terminal 55. For example, various reports can be created using a database report manager to identify those package identifiers that have been previously queried, those which have never been queried, etc. The printer can also be used to generate alarm reports. Alarm reports are essentially reports that are autonomously generated based on a pre-established criteria and algorithms. For example, the printer may generate a list of all packages that have reached their expiration date. Alternatively, the printer can generate reports based on a single POS/POD location generating an abnormal level of authentication requests— such as for a specific drug type. Alternatively, a manufacturer could detect a level of authentication queries that is not commensurate with the level of drugs purchased by the POD/POD. This may potentially highlight abnormal drug handling activities. Finally, the reports may be of other types, such as marketing reports indicating which POD originate which and how many queries. Further, if packages are authenticated at various points in the supply chain, the queries allow determination of the supply route distribution scheme used in handling the drugs.

Figure 6:
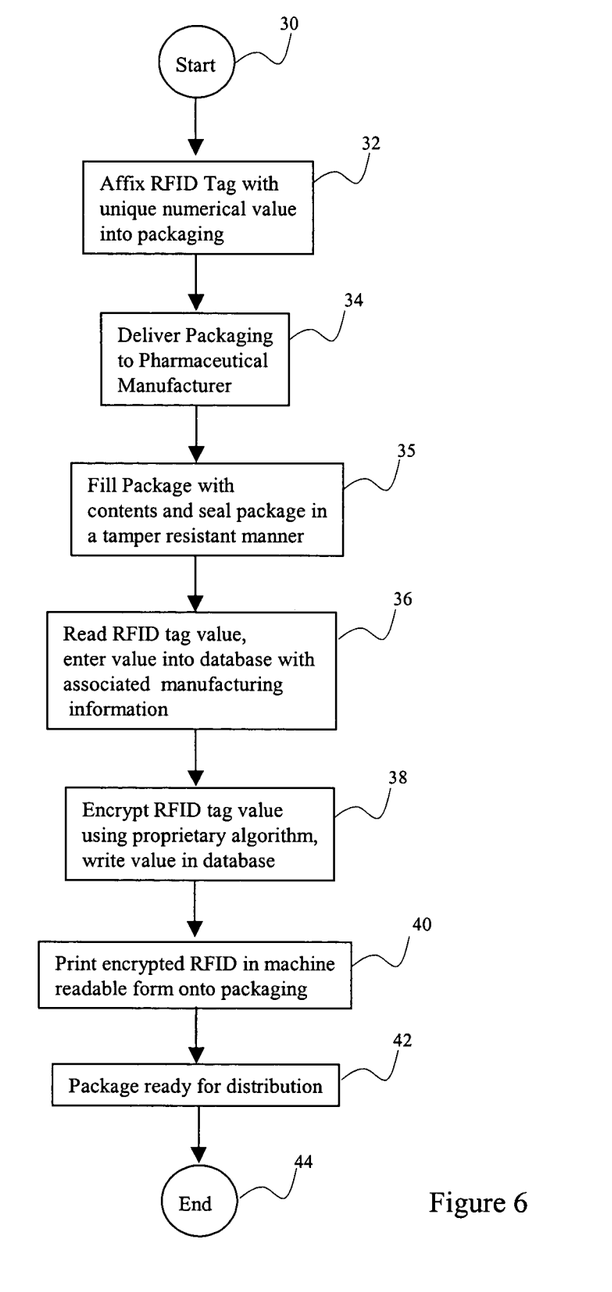
FIG. 6 illustrates one embodiment of a process flowchart for packaging the pharmaceutical drugs in according to the principles of the present invention.

Next, the process for creating a package and establishing the authentication data is described. This process is described in FIG. 6 and illustrates the activities that occur prior to the package being introduced in the various channels of distribution. In FIG. 6, the process begins at step 30 followed by the attachment of an RFID tag to the package at step 31. The RFID tag is a small integrated circuit that can store typically a 32 or 64 byte number. The RFID tag can be 'read-only' (essentially written once), or it can be a 'read/write' (essentially written more than once). The tags are typically small enough that they can be unobtrusively affixed to the package in a variety of ways. Some methods include embedding them into the package at the time of manufacturing of the package, affixing the tag to the package after manufacturing of the package by using adhesive or tape, or affixing the tag to a label that is then affixed to the package. Regardless of the manner in which the tag and package are conjoined, the two are considered 'affixed.'

The RFID tag can be affixed to the package by the package manufacturer. Alternatively, the RFID tag may be affixed to the package by the pharmaceutical manufacturer. The value of the tag can be sequential or random, as long as the same value is not used for different packages. The use of sequential values facilitates indexing records in the manufacturing database.

Next, the package with the RFID tag is delivered to the pharmaceutical manufacturer in step 34. The pharmaceutical manufacturer then fills the package with the appropriate drugs in step 35 and seals the package according to the various techniques so as to discourage and detect tampering. These techniques include various seals and wrappers around the package so that once the package is opened, it is readily detectable. (Although this step is shown in the figure as occurring prior to the next step, the order can be altered.)

Next, the pharmaceutical manufacturer reads the RFID tag value in step 36. The manufacture employs an RFID tag reader similar to the one that may be used at the POS/POD. The package identifier value is entered into the manufacturing database along with additional information associated with the pharmaceutical. The additional information may be recorded at this point in time, or may be entered at a latter time. The information comprising a manufacturing record (a.k.a. package record or package manufacturing record) in the manufacturing database will be discussed shortly, but typically includes information such as the date of manufacturer, expiration date of the drug, nature of the drug, manufacturing plant, etc. The RFID tag value is used as an index for the package manufacturing record. For this reason, a sequential RFID value facilitates accessing the information in the database.

The next step 38 involves encrypting the RFID value to produce the authentication value. A variety of encryption algorithms can be used to produce the authentication data and this is discussed in detail subsequently. Once the authenticating data is determined, the next step 40 involves printing the authenticating value in a machine readable form onto the package, typically on the package's label. One embodiment of a machine readable form involves a one or two dimensional bar code or other optically based scan code. The scanning code can be printed directly onto the package, onto a label on the package, or onto a separate label that is then affixed to the package. Alternatively, other forms of machine readable indicia could be used, such as magnetic inks, text designed for optical character recognition, or write-able RFID tags, including the same tags use for indicating the package identifier. No limitation is implied by the term "affixed" as to how the authenticating indicia appears on the package. At this point, step 42 indicates that the package is ready for distribution and introduction into the supply chain at which point the process is completed 44.

Figure 7:
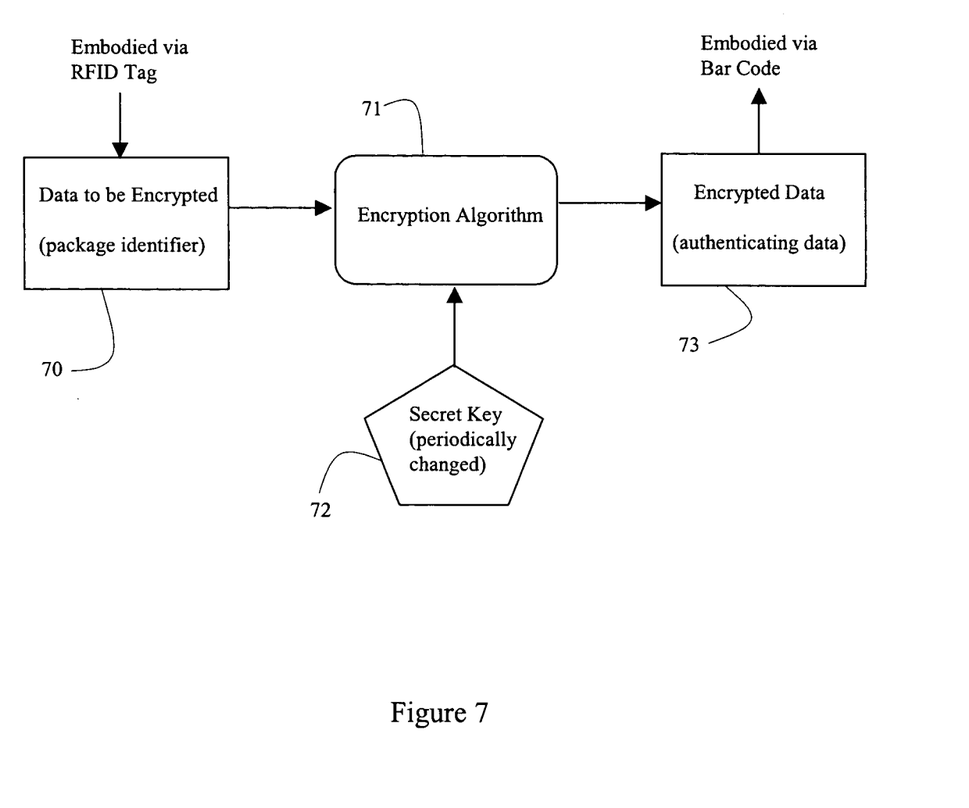
FIG. 7 illustrates one embodiment of the encryption algorithm in accordance with the principles of the present invention.

The determination of the authenticating data is further illustrated in the embodiment of FIG. 7. There are a variety of techniques that can be used for producing authenticating data, and FIG. 7 only illustrates one approach. This approach is based on a well known symmetrical key encryption technique, however in this case, only the manufacturing entity knows the encryption key (algorithm). Further, the manufacturing entity can alter the encryption key at will. The manufacturing entity is required to identify the algorithm used for a given package identifier value.

In FIG. 7, the data to be encrypted 70 is based on the input from the package identifier from the RFID tag value. This data may be equal to the RFID value, or can be the RFID tag value appended with additional information, such as manufacturing specific information (e.g., date of manufacture). This RFID value is typically obtained when reading the RFID tag on the package at or near the time of filling the package, but can be read at other times or processed based on a computer file of package identifiers associated with the RFID tags. In other words, the package identifiers values can be loaded into the manufacturing database prior to filing of the packages, and even loaded before the empty packages are in possession of the drug manufacturer. The encryption algorithm can be any number of algorithms, such as the Digital Encryption Standard, Pretty Good Privacy, or other technique. These techniques are often based on the division of a value into a given polynomial with the remainder value as the encrypted value. The determination of the encrypted value is based in part on a secret key 72, which in this case is known only to the manufacturer. Since there is no need for another party to 'decrypt' information, there is no need for another party to know the key used. The key value can be periodically changed, e.g., every week, so that even if the key is compromised, it will have a limited life span. The manufacture must account for the encryption key and algorithm used for each package identifier, and this can be maintained in the manufacturing database that maintains records for each package identifier. After the package identifier is processed by the algorithm, the encrypted data generated is used as the authenticating data. The authenticating data is typically printed on a label in machine readable form and affixed to the package. Although the package identifier could have the authenticating data affixed to the package prior to filling the package, this increases the risk that the packages with authenticating data could be diverted and passed off as authenticated. Therefore, the authenticating data are typically placed on the package at the time the contents are filled and sealed.

Consequently, this embodiment relies on the input (package identifier) to the encryption process and the output (authenticating data) to be readily determinable from the package. Thus, possession of the package does not facilitate determination of the algorithm or the key. Consequently, possession of an authentic package does not facilitate or aid in creating a counterfeit package. At most, a replicated package can be made, but after the authentic package is sold, any duplicates will be detected upon subsequent authentication. Since the manufacturer only knows the algorithm and the key, only the manufacturer can verify that the authenticating data and the package identifier correspond. In general, the longer the various values that are used (e.g., input, encryption key) and the more complex the encryption algorithm used, the more robust the protection that is afforded. Consequently, it is possible to increase the security by increasing the RFID value. Although 32 or 64 bytes may be used, longer values or more complicated encryption schemes may be used for certain applications.

Figure 8:
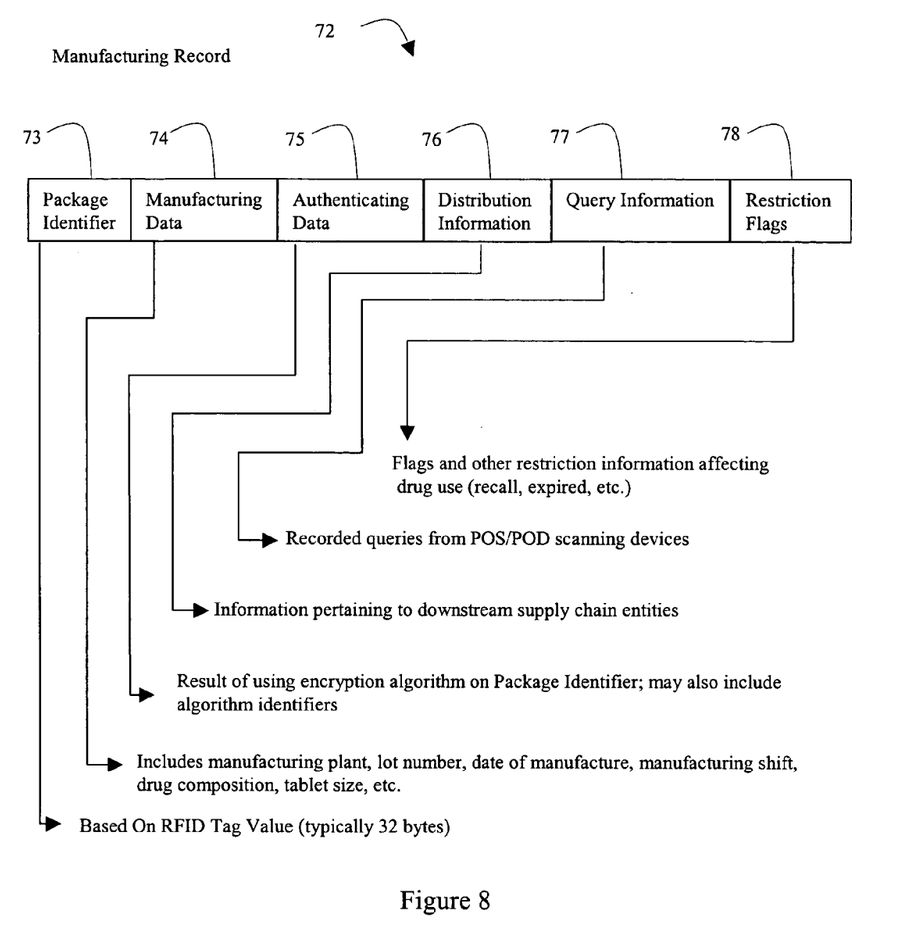
FIG. 8 illustrates one embodiment of a sample record in the authentication database.

FIG. 8 illustrates one embodiment of the contents of a manufacturing record 72 maintained in the manufacturer's database. The first field contains a package identifier 73 that is used to index the record. The package identifier may correspond to the RFID tag or some other value based in part on t RFID value. The package identifier's length typically corresponds to the length conveyed by the RFID tag (e.g., 32 or 64 bytes) and should be sufficiently long enough to avoid replication. The subsequent fields may appear in different order, and the order presented in the embodiment of FIG. 7 is not intended to be limiting. Further, sub-fields may be defined, or pointers to other records in the database may be used. Those skilled in the art will recognize that great flexibility is possible when defining database structures.

The next field is the manufacturing data field 74 indicating manufacturing related information pertaining to the package contents in association with the package identifier, including the drug name and composition, lot number, manufacturing plant, manufacturing shift (e.g., morning or afternoon), expiration date, tablet size or concentration, etc. Text information that is provided in the authentication response and displayed may be derived from this field.

The next field is the authenticating data field 75. This contains the value of the authenticating data. It is the result of applying the encryption algorithm on the package identifier, although numerous other encryption algorithms may be employed. The authenticating data field may also include an identifier indicating which of a plurality of algorithms was used. Alternatively, a separate field may be used. This allows the manufacture to use different encryption algorithms and record which algorithm was used for this particular package identifier.

The next field is the distribution information field 76. This contains information regarding the downstream supply chain associated with this drug. For example, the wholesaler or distributor that this drug was manufactured for (or sent to) can be indicated here.

The next field is the query information field 77. This information is blank at the time the record is created, and contains information associated with the subsequent receipt of an authenticating query. The query information field may indicate the date, origin or the query, and the response provided. This information can be used to determine whether a particular package was sold or dispensed. It can also be used to track down remaining unsold or non-dispensed packages should a defective manufacturing lot be subsequently discovered. Many other applications, including data mining, marketing studies, et cetera, can be derived by analysis of the query information field.

Finally, the last field typically contains restriction flags 78. These flags may be set if conditions arise which effect the sale or dispensing of the drug. For example, flags may be set if the drug is found to be defective, a shipment is reported to be stolen or lost, or if the current date is beyond the expiration date of the drug. These flags may correspond to various text messages that are generated and displayed in the query response and may indicate reasons why the package should not be sold or dispensed. For example, a pharmaceutical manufacturer may set the flags for all unqueried packages once the expiration date has passed. Then, if an query requesting authentication is received, the flag would deny sale or dispensing of the drug based on it being past the expiration date.

Figure 9:
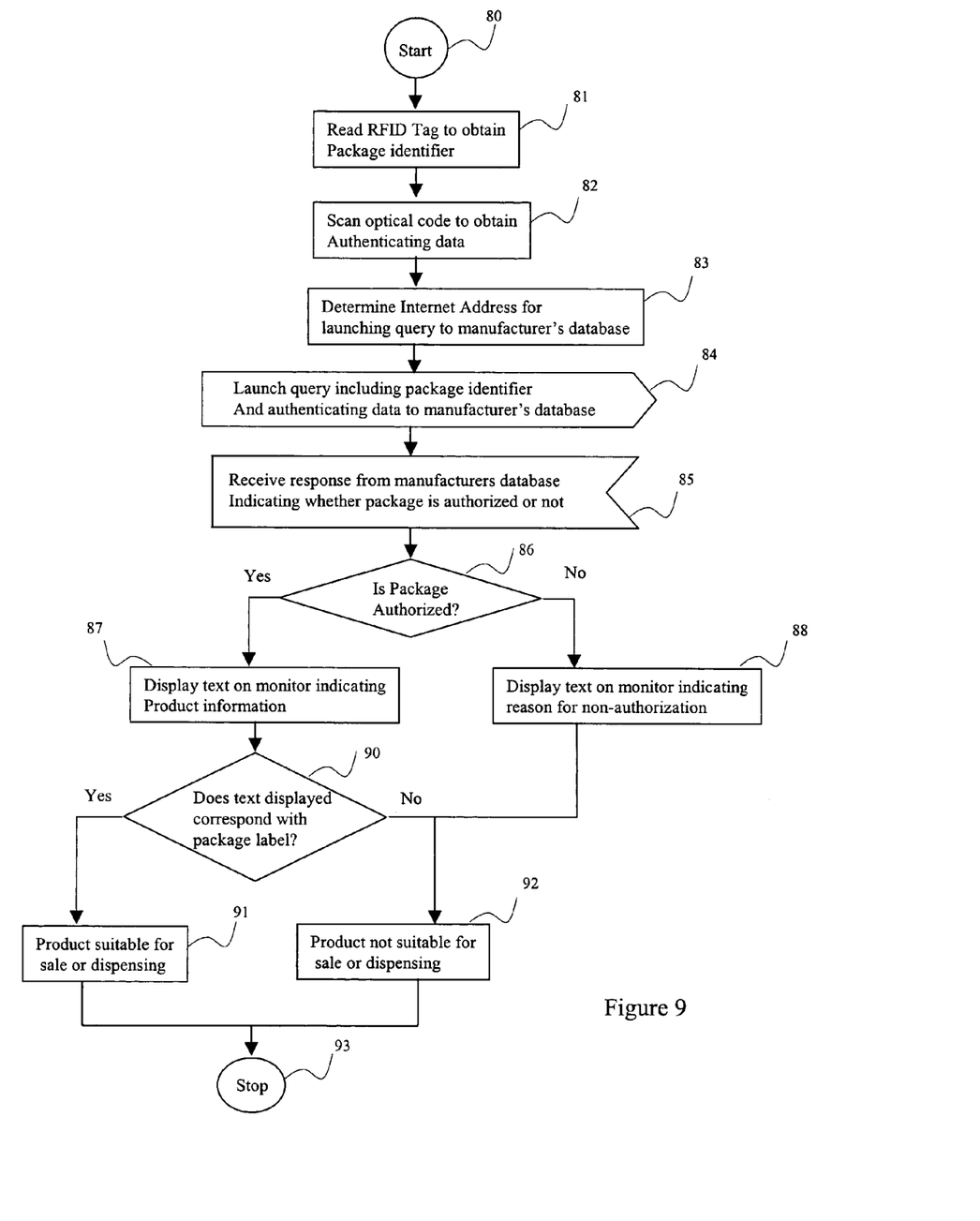
FIG. 9 illustrates one embodiment of an authentication process according to the principles of the present invention.

Once introduced into the supply chain, the package ultimately reaches a point where it is ready to be dispensed or sold. While the package can be authenticated prior to the sale or dispensing, determining whether the package is authentic is most effective when performed just prior to being sold or dispensed. The processing steps to authenticate the package prior to sale or dispensing are similar as authenticating a package when it is currently sold or dispensed. FIG. 9 illustrates the steps involved when the package is authenticated.

In FIG. 9, the process starts at step 80 when authorized personnel selects the package for sale or dispensing and then reads the RFID tag at step 81. The RFID tag is read to determined the package identifier. Next, the optical code representing the authenticating data is scanned at step 82. This step could occur prior to reading the package identifier. Regardless of the order, once the package identifier and authenticating data is determined, the appropriate Internet address for launching a query to the manufacturer's database is determined in step 53. The address can be determined using the aforementioned techniques and the address is used to direct the query that occurs in step 84. The query includes at least both the package identifier and authenticating data. It may also indicate the point of origin as well. The system then waits for a response, and the response is received in step 85. The response indicates whether the package is authorized or not. If the package is not authorized as indicated in step 86, then a text message is displayed on the system monitor at step 88 indicating the package is not authorized for sale or dispensing. The response may further indicate the reason the package is not authorized (e.g., package identifier not found, authenticating data does not match, package contents are recalled, drug has exceeded the expiration date, etc.). Regardless of the reason, the package is determined not suitable for sale at step 92. The process completes at step 93.

If however the package is authorized at step 86, then a text messages is displayed on the monitor including product related information at step 87. At this point, the user involved in initiating the query at the POS/POD should examine the text message on the display and compare the information with the label information at step 90. If the information matches, then the product can be sold or dispensed at step 91. The package is also presumed to be inspected to determine that there is no evidence of tampering. This occurs independent of the authentication query. If there is evidence of tampering (e.g., plastic seal wrap is missing), the product should not be sold regardless of the authentication results. Further, if the information describing the contents of the package does not correspond to the contents of the label on the package, then product is not suitable for sale of dispensing at step 92.

Typically, the POS/POD system records the queries and the responses, as well as the time the query occurred. This provides a record of the transaction, and can be useful to forensically determine whether the package was authenticated or not.

Figure 10:
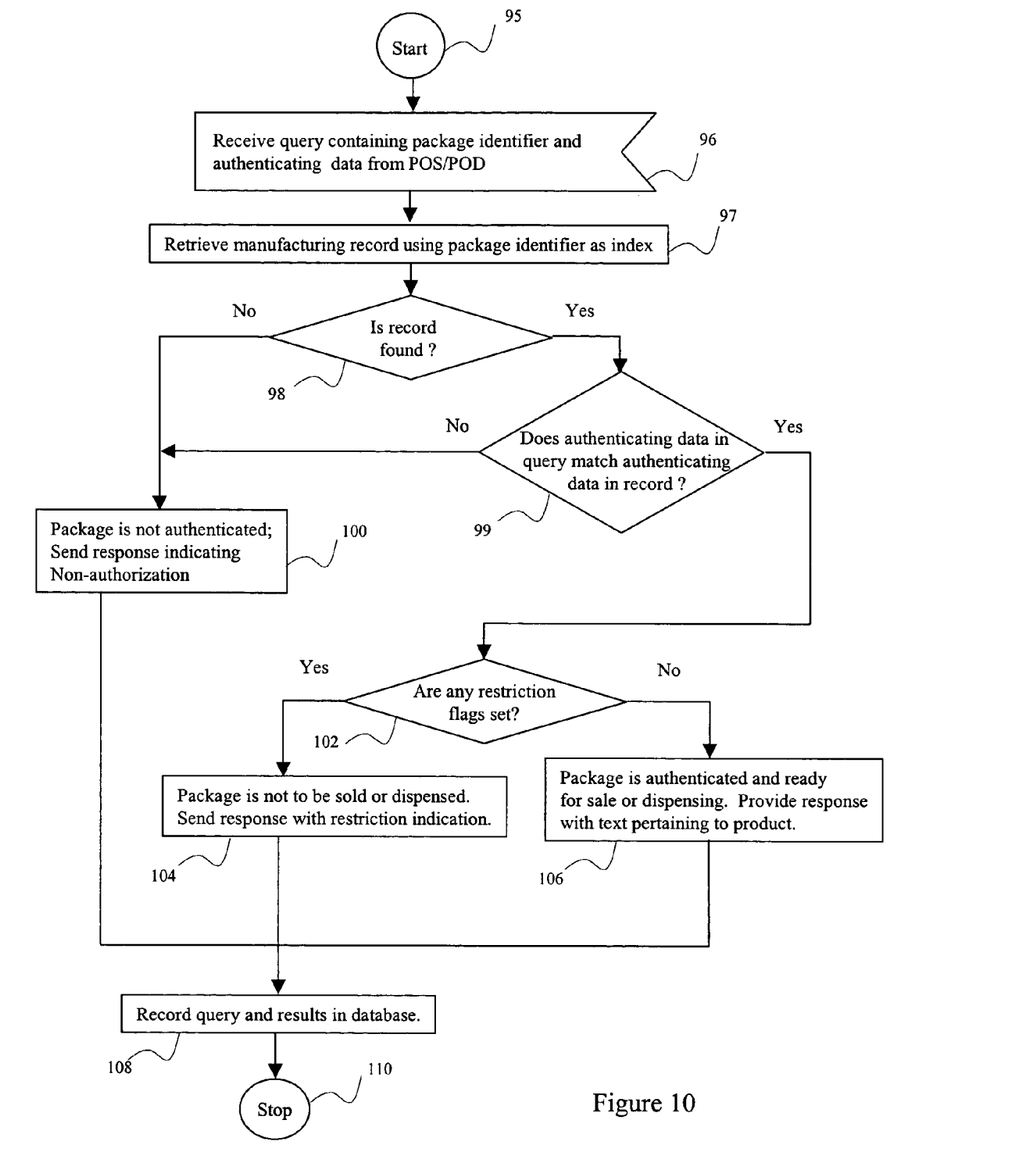
FIG. 10 illustrates one embodiment of the authentication database process for responding to an authentication request according to the principles of the present invention.

The processing of a query is also embodied from the perspective of the manufacturer's database in FIG. 10. In FIG. 10, the process begins in step 95 with the manufacturer's database receiving a query in step 96. The query contains the package identifier and the authenticating data from a POS/POD. Although not shown, the query may contain identifying data of the POS/POD as well as authenticating information verifying the identify of the POD/POS. Various security and authentication schemes for identifying the origin can be used. In step 97, the database retrieves the corresponding manufacturing record using the package identifier as an index. At step 98, the system tests whether the record is found. If the record is not found, then the package is not authentic, or at least an error has occurred rending the package suspect. The response indicates the package is not authorized in step 100. Assuming the record is found, then at step 99, the system checks whether the authenticating data in the query matches the authenticating data in the database. If the results match, then the system proceeds to step 102 where any restriction flags are set. If restrictions flags are set (e.g., the expiration date of the drug has passed), then in step 104 the response is sent with information indicating the type of restriction. If no restriction flags are set, then in step 106 the system provides a response that the product may be sold/dispensed. In all cases, the query and the response are typically recorded in the database in step 108. This facilitates analysis of various situations and conditions. Finally, at step 110, the process for the query is completed.

The present invention is not limited to detecting authenticating packaged pharmaceuticals, but can authenticate a package containing any type of contents. For example, a package may contain precious metals or jewels, specifically designed machine parts, semiconductors, etc. Further, the principles of the present invention may apply to products directly bearing the identification and authenticating indicia. For example, discount coupons, vouchers, checks, et cetera may have both indicia printed onto the coupon or voucher that could be used to determine authenticity. Securities documents, checks, and credit cards could bear both indicia. For example, a credit card may have authenticating data encoded on the magnetic strip and included when authorization for a charge occurs.

I claim:

1. A method for authenticating the contents of a package, comprising:
   reading a first value associated with the package, from a radio frequency identification (RFID) tag, using a first input device operatively connected to a processing system, the first value comprises a package identifier;
   reading a second value, associated with the package, from a machine-readable optical code, said second value being generated, at least based in part, on the package identifier;
   formulating a query by the processing system, the query including said first value and said second value;
   sending the query to a manufacturing database maintained by a manufacturer that produces the contents;
   receiving a response, to the query, from the manufacturing database indicating whether the contents of the package are authentic based on determining, via a processor whether the first value matches a corresponding third value in the database and whether the second value matches a corresponding fourth value in the database; and
   displaying text based on a computer monitor operatively connected to the processing system, the text based in part on the received response, the text including a description of the contents of the package.

2. The method of claim 1 wherein the second value is read using a second device incorporating an optical scanner, the second device operatively connected to the processing device.

3. The method of claim 1 wherein the second value is determined using the first input device.

4. The method of claim 1 wherein the contents of the package are pharmaceuticals and the response further indicates conditions pertaining the use of the pharmaceuticals.

5. The method of claim 4 wherein the text displayed on the computer monitor indicates the package should not be dispensed or sold.

6. The method of claim 1 wherein the text displayed on the computer monitor replicates information indicated on a label affixed to the package.

7. The method of claim 1 wherein the package contains one or more from the group of pharmaceuticals, documents, credit cards, precious metals, gemstones, electronics, or medical supplies.

8. The method of claim 1 wherein the processing system is a point of sale terminal.

9. The method of claim 1 wherein the query is sent to an Internet address determined in part on a indicia associated with the package representing a national drug code.

10. The method of claim 1, wherein prior to displaying text, the method further comprises:
    receiving an indication in the response specifying that the contents are not salable or dispensable when determining, via the processor, that at least the first value is linked to information in the database indicating at least one restriction even when the contents are determined to be authentic.

11. A system for authentication of one or more pharmaceuticals, comprising:
    a radio frequency identification (RFID) tag reader configured to read an RFID tag affixed to a pharmaceutical package, the RFID tag reader providing a first value comprising a package identifier;
    an optical reader for reading an optical code affixed to the pharmaceutical package, the optical reader providing a second value, the second value being generated, based in part, on the package identifier; and
    a data processing system comprising a display, the data processing system operatively connected to the RFID reader and the optical reader, the data processing system receiving the first value and the second value, the data processing system further configured to send a query containing the first value and the second value over a communications network to a manufacturing database that is maintained by a manufacturer that produces the pharmaceuticals, the data processing system configured to:
    receive a response, to the query, from the manufacturing database indicating whether the pharmaceutical package is authenticated based on determining, via a processor, whether the first value matches a corresponding third value in the database and whether the second value matches a corresponding fourth value in the database; and
    display a text message on the display based in part on the response.

12. The system of claim 11 wherein the data processing system is configured to provide point-of-sale processing.

13. The system of claim 11 wherein the data processing system includes an interface to the Internet for conveying the query.

14. The system of claim 11, wherein the data processing system is further configured to:
    receive an indication in the response specifying that the pharmaceuticals are not salable or dispensable when a determination reveals that at least the first value is linked to information in the database indicating at least one restriction even when the pharmaceutical package is determined to be authentic.

15. A system comprising:
    a first device configured to read a machine-readable indicia from a radio frequency identification (RFID) tag affixed to a package containing one or more pharmaceuticals providing a first numerical value comprising a package identifier;
    a second device configured to read a machine-readable optical code affixed to the package providing a second numerical value that is generated, based in part, on the package identifier;

a processor operatively connected to the first and second device configured to receive and store the first and second numerical values;

generate a query incorporating the first and second numerical values along with identification data associated with the processor;

use a communications network to transmit the query to a manufacturing database;

receive a response, to the query, from the manufacturing database comprising confirmation data indicating whether the first numerical value matches a corresponding third numerical value stored in the database and the second numerical value matches a corresponding fourth numerical value stored in the database;

store the confirmation data in a memory, the processor further configured to provide a visual indication of the confirmation data; and a display operatively connected to the processor receiving the signal indicating the confirmation data and displaying a confirmation message to a user.

16. The system of claim 15, wherein in response to the processor evaluating data in the manufacturing database and determining that the first numerical value does not match the third numerical value and that the second numerical value does not match the fourth numerical value, the confirmation data generated by the processor indicates that the pharmaceuticals are not authentic and should not be dispensed or sold.

17. The system of claim 15, wherein the processor is further configured to:

receive an indication in the response specifying that the pharmaceuticals are not salable or dispensable when a determination reveals that at least the first numerical value is linked to information in the manufacturing database indicating at least one restriction even when the confirmation data comprises content indicating that the pharmaceuticals are determined to be authentic.

* * * * *